United States Patent
Zhao et al.

(10) Patent No.: US 10,149,903 B2
(45) Date of Patent: Dec. 11, 2018

(54) FULLY HUMAN ANTIBODY AGAINST RESPIRATORY SYNCYTICAL VIRUS

(71) Applicant: EliteImmune Inc., Tianjin (CN)

(72) Inventors: Xuelian Zhao, Tianjin (CN); Guohua Liu, Tianjin (CN); Quanying Wang, Tianjin (CN)

(73) Assignee: ELITEIMMUNE INC., Tianjin (CN)

( * ) Notice: Subject to any disclaimer, the term of this patent is extended or adjusted under 35 U.S.C. 154(b) by 0 days.

(21) Appl. No.: 15/990,999

(22) Filed: May 29, 2018

(65) Prior Publication Data

US 2018/0264103 A1    Sep. 20, 2018

Related U.S. Application Data

(63) Continuation of application No. PCT/CN2016/107658, filed on Nov. 29, 2016.

(30) Foreign Application Priority Data

Nov. 30, 2015   (CN) .......................... 2015 1 0867051
Nov. 23, 2016   (CN) .......................... 2016 1 1036424

(51) Int. Cl.
| | |
|---|---|
| *A61K 39/395* | (2006.01) |
| *A61K 39/42* | (2006.01) |
| *A61K 39/00* | (2006.01) |
| *C07K 16/10* | (2006.01) |
| *C07K 16/00* | (2006.01) |
| *A61K 39/295* | (2006.01) |
| *C12N 15/63* | (2006.01) |
| *A61P 31/14* | (2006.01) |

(52) U.S. Cl.
CPC .......... *A61K 39/295* (2013.01); *A61K 39/395* (2013.01); *A61P 31/14* (2018.01); *C07K 16/00* (2013.01); *C07K 16/1027* (2013.01); *C12N 15/63* (2013.01); *A61K 2039/55* (2013.01); *A61K 2039/6075* (2013.01); *C07K 2317/21* (2013.01)

(58) Field of Classification Search
CPC .......... A61K 2039/505; C07K 16/1027; C07K 2317/24; C07K 2317/565; C07K 2317/76
See application file for complete search history.

(56) References Cited

U.S. PATENT DOCUMENTS

2005/0175986 A1    8/2005    Gross

FOREIGN PATENT DOCUMENTS

| CN | 1986569 A | | 6/2007 |
| CN | 101808663 A | | 8/2010 |
| CN | 106496324 | * | 3/2017 |
| WO | WO2011020079 A1 | | 2/2011 |
| WO | WO2011043643 A1 | | 4/2011 |
| WO | WO2015006596 A2 | | 1/2012 |
| WO | WO2013095091 A2 | | 6/2013 |
| WO | WO2014159822 A2 | | 10/2014 |
| WO | WO2014170258 A1 | | 10/2014 |

OTHER PUBLICATIONS

Search Report for EP Application No. 168699551 dated Jun. 27, 2018.
WO2014159822A3—ISR involved in Search Report for EP Application No. 168699551 dated Jun. 27, 2018.
WO2013095091A3—ISR involved in Search Report for EP Application No. 168699551 dated Jun. 27, 2018.
WO2012006596A3—ISR involved in Search Report for EP Application No. 168699551 dated Jun. 27, 2018.
Laurent Detalle et al involved in Search Report for EP Application No. 168699551 dated Jun. 27, 2018.
J. E. Schuster et al involved in Search Report for EP Application No. 168699551 dated Jun. 27, 2018.
International Search Report for PCT/CN2016/107658 dated Jan. 26, 2017.
Written Opinion of the International Searching Authority for PCT/CN2016/107658 dated Jan. 26, 2017.

* cited by examiner

*Primary Examiner* — Barry A Chestnut
(74) *Attorney, Agent, or Firm* — Flener IP & Business Law; Zareefa B. Flener

(57) ABSTRACT

Disclosed are an antibody (preferably a fully human antibody R66) against respiratory syncytical virus RSV, encoding nucleic acids thereof, a vetor and a host cell comprising the same, and a preparation method thereof. Disclosed are also a use of the antibody (preferably a fully human antibody R66) against RSV in the prevention and treatment of RSV-related diseases, and a use of the same in detecting TSV. The above antibody against RSV is preferably a fully human monoclonal antibody. Compared with other animal-derived (e.g., murine) anti-RSV antidodies, the immunogenicity caused by species differences is greatly reduced. With good specificity and affinity, if used for clinic, it will greatly reduce side effects.

12 Claims, 3 Drawing Sheets

Specification includes a Sequence Listing.

FULLY HUMAN ANTIBODY AGAINST RESPIRATORY SYNCYTICAL VIRUS

CROSS-REFERENCE TO RELATED APPLICATION

This application is a continuation application of International patent application No. PCT/CN2016/107658, filed on Nov. 29, 2016, which claims the benefit and priority of Chinese patent applications No. CN 201510867051.9, filed on Nov. 30, 2015, and CN 201611036424.9, filed on Nov. 23, 2016, each of which is incorporated herein by reference in its entirety and for all purposes.

FIELD OF THE INVENTION

The present invention relates to an antibody against respiratory syncytical virus or an antigen-binding fragment thereof, in particular to a fully human monoclonal antibody against respiratory syncytical virus (RSV).

BACKGROUND OF THE INVENTION

A humanized antibody can be prepared by replacing the regions in a mouse antibody that are not critical for antigen specificity with a human counterpart. The resulting recombinant antibodies thus have residual murine sequences which, when administered to a human patient, often elicit immunological responses in the patient (human anti-murine response). Therefore, it is desirable to prepare fully human antibodies that are void of non-human sequences. Fully human antibodies have been reportedly obtained, such as by constructing and screening a human antibody library using the phage display technology, by grafting lymphocytes from immunized human donors into severe combined immunodeficient (SCID) mice, or by engineering transgenic mice harboring human immunoglobulin genes. Fully humanized human antibodies against pathogens can also be obtained by isolation of umbilical cord blood containing a natural polyreactive IgM repertoire through extensive screening (see, for example, U.S. Pat. No. 6,391,635). These methods, however, either produce antibodies with low affinities or depend on human donors with a desired immune response.

Respiratory syncytial virus (RSV, also known as syncytial virus, also belonging to Paramyxoviridae) is the most common cause of viral pneumonia in children, which may cause interstitial pneumonia and bronchiolitis. 48% of viral pneumonia and 58% of bronchiolitis in Beijing (1980-1984), 31.4% of pneumonia and bronchiolitis in children in Guangzhou (1973-1986) and 20% to 25% of infant pneumonia and 50% to 75% of bronchiolitis in the United States are caused by the syncytial virus.

The RSV infection has an incubation period of 2 to 8 days (mostly 4 to 6 days). Typical pathological changes of syncytial virus pneumonia are interstitial infiltrates of monocytes, which are mainly characterized by widened alveolar septa and interstitial effusion, mainly monocytes including lymphocytes, plasma cells, and macrophages. In addition, the alveolar space is filled with edema fluid and the formation of a transparent membrane in the lung can be observed. In some cases, lymphocytic infiltration of the bronchiole wall can be further observed. The presence of edema in the lung parenchyma with necrotic areas leads to alveolar packing, consolidation, and collapse. In a few cases, multinucleated fusion cells can be observed in the alveolar space, whose morphology is similar to that of measles giant cells, but no nuclear inclusion bodies could be found.

RSV has two major surface glycoproteins, F and G. The two glycoproteins (90 KDa and 68 KDa) respectively are presented on the surface of the virus particles. The highly glycosylated G protein, 90 KDa, is responsible for the binding of viral particles to host cells. The glycoprotein F, 68 KDa, mediates viral cell membrane fusion and syncytia formation. The surface glycoproteins F and G are the major protective antigens, while nucleoprotein N and envelope protein M2 have less protective antigenicity. Compared with monoclonal antibodies against glycoprotein F, monoclonal antibodies against glycoprotein G are less likely to neutralize viruses and have no fusion inhibiting activity. The amino acid sequence of the glycoprotein F is approximately 90% conserved among the RSV strains associated with human infection.

The sole anti-RSV monoclonal antibody currently on the market is only approved for the prevention of RSV infection in preterm infants, which is a humanized monoclonal antibody against the glycoprotein F with name of Palivizumab Synagis (Made by MedImmune). The drug prevents the virus from spreading to the lower respiratory tract through respiratory syncytial virus fusion protein (glycoprotein F).

SUMMARY OF THE INVENTION

The object of the present invention is to provide an anti-RSV antibody or an antigen-binding fragment thereof, preferably a fully human anti-RSV monoclonal antibody and an antigen-binding fragment thereof.

According to an aspect of the present invention, an anti-RSV antibody or an antigen-binding fragment thereof is involved, wherein the antibody comprises:

at least one heavy chain CDR having an amino acid sequence selected from the group consisting of SEQ ID NO: 6, SEQ ID NO: 8, and SEQ ID NO: 10; and/or at least one light chain CDR having an amino acid sequence selected from the group consisting of SEQ ID NO: 12, SEQ ID NO: 14, and SEQ ID NO: 16.

Further, for the antibody or antigen-binding fragment thereof, wherein the antibody comprises:

three heavy chain CDRs selected from those having the amino acid sequences as shown in SEQ ID NO: 6, SEQ ID NO: 8, and SEQ ID NO: 10; and/or three light chain CDRs selected from those having the amino acid sequences as shown in SEQ ID NO: 12, SEQ ID NO: 14, and SEQ ID NO: 16.

Preferably, the antibody or antigen-binding fragment thereof comprises:

a heavy chain variable region having the amino acid sequence as shown in SEQ ID NO: 3 and/or a light chain variable region having the amino acid sequence as shown in SEQ ID NO: 4, and the antibody is a fully human anti-RSV monoclonal antibody R66.

Optionally, the antigen-binding fragment of the present invention is selected from the group consisting of Fab, Fab', F(ab)$_2$, single chain Fv(scFv), Fv, dsFv, diabody, Fd, and Fd' fragments.

According to another aspect of the present invention, a fully human anti-RSV monoclonal antibody R66 is involved. The nucleic acid sequences of the heavy chain and light chain (kappy) of the monoclonal antibody R66 are as shown in SEQ ID NO: 1 and SEQ ID NO: 2, respectively, and the corresponding amino acid sequences of the heavy chain and light chain (kappy) are as shown in SEQ ID NO: 3 and SEQ ID NO: 4, respectively.

The present invention also relates to an antibody derived from the antibody R66 described above by insertion, substitution and/or deletion within the heavy chain and/or light chain amino acid sequence and having the same function of the antibody R66.

The present invention also relates to an antigen-binding fragment of the aforementioned antibody R66, in particular to an antigen-binding fragment selected from the group consisting of Fab, Fab', F(ab)$_2$, single chain Fv(scFv), Fv, dsFv, diabody, Fd, and Fd' fragments.

The present invention also relates to a single domain antibody, a chimeric antibody, a antibody fusion protein, an antibody/antibody fragment-factor fusion protein or antibody/antibody fragment-chemical conjugate containing a single heavy chain and/or a single light chain of the antibody described above, preferably R66.

The present invention provides a nucleic acid encoding the above antibody, which comprises:

at least one nucleotide sequence encoding the heavy chain CDR selected from the group consisting of SEQ ID NO: 5, SEQ ID NO: 7 and SEQ ID NO: 9; and/or at least one nucleotide sequence encoding the light chain CDR selected from the group consisting of SEQ ID NO: 11, SEQ ID NO: 13 and SEQ ID NO:15.

Preferably, the nucleic acid of the present invention comprises:

a nucleic acid as shown in SEQ ID NO: 1 encoding the heavy chain variable region and/or a nucleic acid as shown in SEQ ID NO: 2 encoding the light chain variable region.

According to another aspect of the present invention, a method for preparing an anti-RSV antibody, preferably a fully human anti-RSV monoclonal antibody, is provided, comprising the following steps:

(1) providing an expression vector comprising a DNA molecule encoding the anti-RSV antibody, preferably the fully human anti-RSV monoclonal antibody, of the present invention, and an expression regulatory sequence operably linked to the DNA molecule;

(2) transforming a host cell with the expression vector;

(3) cultivating the host cell under conditions suitable for expression of the anti-RSV antibody, preferably the fully human anti-RSV monoclonal antibody; and (4) separating and purifying to obtain the anti-RSV antibody, preferably the fully human anti-RSV monoclonal antibody.

According to another aspect of the present invention, a vector comprising a nucleic acid sequence of the anti-RSV antibody, preferably the fully human anti-RSV monoclonal antibody of the present invention and a host cell comprising the nucleic acid sequence or the vector are provided.

The vector may be a recombinant expression vector.

The host cells may be 293T cells, Chinese hamster ovary (CHO) cells, NS0, SP2 cells, HeLa cells, baby hamster kidney (BHK) cells, monkey kidney cells (COS), human liver cancer cells, 549A cells, 3T3 cells, and many other cell lines.

According to another aspect of the present invention, the use of the anti-RSV antibody (preferably the fully human anti-RSV monoclonal antibody), the nucleic acid, vector or host cell of the present invention in the preparation of a therapeutic agent for preventing or treating RSV-related diseases is provided.

According to another aspect of the present invention, a pharmaceutical composition for treating RSV-associated diseases is provided, wherein the pharmaceutical composition comprises a therapeutically effective amount of the anti-RSV antibody (preferably the fully human anti-RSV monoclonal antibody), nucleic acid, vector or host cell of the present invention, and one or more pharmaceutically acceptable carriers or excipients. The pharmaceutically acceptable carriers or excipients are well known to those skilled in the art and include physiologically compatible aqueous and non-aqueous vehicles, stabilizers, preservatives, solubilizers, antioxidants, solvents, dispersion media, coatings, buffers, serum proteins, and the like.

The RSV-associated disease is selected from the group consisting of viral pneumonia, interstitial pneumonia, and bronchiolitis.

According to another aspect of the present invention, the use of the anti-RSV antibody (preferably the fully human anti-RSV monoclonal antibody), the nucleic acid, vector or host cell of the present invention in the preparation of a detection reagent for detecting RSV is provided.

The anti-RSV antibody (preferably anti-RSV monoclonal antibody) provided by the present invention is preferably fully human antibody, and compared to other animal-derived (eg, mouse-derived) anti-RSV antibodies, it has greatly reduced immunogenicity caused by species differences, high specificity and affinity, and if used for clinic, it may greatly reduce side effects. In addition, the anti-RSV antibody (preferably a monoclonal antibody) in the present invention also may have excellent performance in the diagnosis and detection of RSV since it can specifically bind to the antigen F of RSV. When applied to humans, it does not produce side effects resulted from murine antibodies.

DETAILED DESCRIPTION OF THE INVENTION

Figure 1:
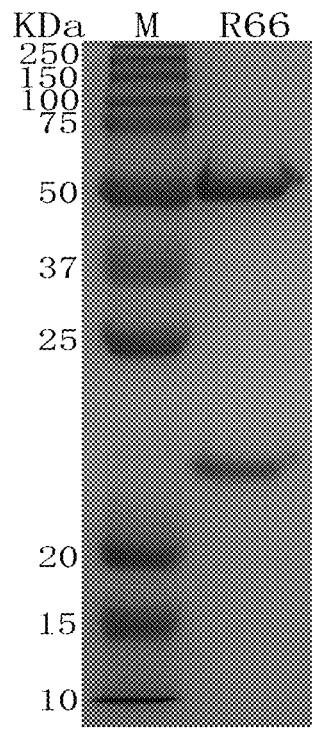
FIG. 1 shows an electropherogram of R66 after purification.

To make the objectives, technical solutions, and advantages of the present invention clearer and more comprehensible, the following further describes the present invention in detail with reference to specific embodiments in combination with the accompanying drawings. It should be understood that these descriptions are only exemplary and are not intended to limit the scope of the present invention. In addition, in the following description, descriptions of well-known structures and techniques are omitted so as not to unnecessarily obscure the concept of the present invention.

Example 1 Preparation of Fully Human Anti-RSV Antibody R66

1. Synthesis of Heavy Chain Variable Region and Light Chain Variable Region of R66

The nucleic acid sequence of the heavy chain variable region of the monoclonal antibody R66 as shown in SEQ ID NO: 1 and the nucleic acid sequence of light chain (kappy) variable region of the monoclonal antibody R66 as shown in SEQ ID NO: 2 were synthesized by GENEWIZ Corporation.

The synthesized heavy chain variable region and light chain variable region of R66 were used as templates, Taq enzyme and dNTPs, and primers were added, respectively, and PCR was performed to obtain a PCR product.

2. Construction of Expression Vector for Recombinant Antibody

The PCR product was recovered using a rapid DNA product purification kit (purchased from ComWin Biotech Co., Ltd.) to obtain 40 μl of the PCR product to be used.

The target fragments of the heavy chain variable region and the light chain variable region of R66 were double-digested, respectively. The double-digestion system was as follows: 0.5 μl each of Nhe I and Not I, 3 μl of 10× FastDigest Green Reaction Buffer and 26 μl of PCR product. The resulting mixture was incubated at 37° C. for 5 hours.

The transformed expression vector (the expression vector was pcDNA3.1-Zeo(+) (Invitrogen Corporation), and the constant region of the heavy/light chain of human antibody was previously transformed into this expression vector by GENEWIZ) was double-digested. The double-digestion system was as follows: 0.5 μl each of Nhe I and Not I, 3 μl of 10× FastDigest Green Reaction Buffer, 1 μg of vector, adjusting to 30 μl total volume with $H_2O$. The resulting mixture was incubated at 37° C. for 30 minutes. Then 2 μl of alkaline phosphatase and 3.5 μl of 10× buffer (NEB) were added and mixed. The resulting mixture was incubated in 37° C. water bath for 2 hours.

The Nhe I, Not I, and 10× FastDigest Green Reaction buffer used in the above-described double-digestion system of the target fragment and the vector were all purchased from Thermo Scientific.

The target fragments of the heavy chain variable region and the light chain variable region of digested R66 were respectively subjected to 1% agarose gel electrophoresis, and the results were observed by an UV instrument. The target band was cut and placed in an Eppendorf tube that had been weighed, and each target fragment was recovered using a Rapid Sepharose DNA Recovery Kit (purchased from ComWin Biotech Co., Ltd.).

Each target fragment was respectively ligated into the vector. The ligation system was: 2 μl of the vector, 15 μl of the target fragment, 1 μl of T4 DNA Ligase (purchased from NEB), and 2 μl of buffer. The resulting mixture was incubated in water bath at 16° C. for 2 hours.

All the ligation products of each target fragment were added to *E. coli* DH5α competent cells, mixed gently and ice bathed for 30 minutes, quickly placed in an ice bath for 5 minutes after being heat-shocked at 42° C. for 90 seconds, then added with 800 μL of LB and incubated at 37° C. with shaking (100 rpm) for 1 hour. The culture broth was centrifuged at 10,000 rpm for 15 seconds, 800 ul of the supernatant was removed, and the precipitate was resuspended and all were spread on LB agar plate containing 100 μg/mL ampicillin sodium, and was cultured at 37° C. overnight. A single colony was picked and inoculated into 5 ml of LB containing 100 μg/mL ampicillin sodium, and cultured with shaking at 37° C. for 15 hours. Plasmids were extracted using a Pure Mini Plasmid Kit (purchased from ComWin Biotech Co., Ltd.) to obtain plasmids containing heavy chain (RH66) of R66 and light chain (RK66) of R66, respectively, which were subjected to sequencing.

The sequencing results showed that the nucleic acid sequences of the heavy chain variable region and light chain (kappy) variable region of the monoclonal antibody R66 are as shown in SEQ ID NO: 1 and SEQ ID NO: 2, respectively, and the amino acid sequences of the corresponding heavy chain variable region and light chain (kappy) variable region are as shown in SEQ ID NO: 3 and SEQ ID NO: 4, respectively.

Example 2 Expression and Purification of Monoclonal Antibody R66

293T cells were respectively transfected with the plasmid containing the heavy chain (RH66) of R66 and the plasmid containing the light chain (RK66) of R66 obtained in Example 1. First, the plasmid and PEI were separately diluted with Opti-MEM (1×) buffer, and then the PEI-Opti-MEM mixture was added to a plasmid-Opti-MEM mixture tube dropwise. After standing for 20 minutes at room temperature, the PEI and plasmid mixture was added to a cell suspension. The cell concentration at the time of transfection was 0.25 to 0.5×$10^6$ cells/ml, and 2.5 μg of the plasmid containing the heavy chain of R66+ (in combination with) 2.5 μg of the plasmid containing the light chain of R66+10 μg of PEI were used for transfection of cells per well. After transfection, the supernatant was harvested after being cultured for 48 hours at 37° C., and detected by ELISA.

The expressed antibody protein was purified using rProtein A Sepharose Fast Flow (GE). The culture supernatant of 293T cells expressing R66 was collected by centrifugation at 10,000 rpm, 4° C. for 10 minutes, and added to a rProtein A Sepharose Fast Flow column that have been equilibrated with PBS (20 mM phosphate buffer, 150 mM sodium chloride, pH 7.4). The column was washed with 10 column volumes of the same equilibration buffer followed by 5 column volumes of an elution buffer (0.1 M Gly-HCl buffer, pH 2.5), and the first 3 column volumes of the eluate were collected. A neutralizing solution (1M Tris-HCl buffer, pH 9.0) was added into the collected eluate at a volume ratio of 1/10 and mixed. The resulting mixture was added to an Amicon Ultra-15 Centrifugal Filter (Merck Millipore), and centrifuged at 5000 g, 4° C. for 20 minutes for concentration of protein. The above equilibration buffer was added to the Amicon Ultra-15 Centrifugal Filter, centrifuged at 5000 g, 4° C. for 20 minutes, then new equilibration buffer was replaced, repeated three times to obtain the concentrated protein of the antibody R66, which was transferred to a 1.5 ml centrifuge tube, sampled for determining protein concentration, and then stored at 4° C.

The purified antibody R66 was taken and subjected to electrophoresis. The results are shown in FIG. 1, wherein the lane M is a standard ladder; lane R66 is the purified antibody R66, which has two distinct bands, respectively a heavy chain of about 50 KDa and a light chain of about 22 KDa.

Example 3 ELISA Detection of Antibody R66

The reagents used include:
PBS (1×): prepared with PBS (10×) and deionized water.
PBST: prepared by adding Tween-20 to PBS (1×) to a final concentration of 0.05%.
Blocking solution: PBS (1×)+2% BSA+2% fetal bovine serum (FBS), prepared before use.
Diluent: PBST+1% BSA, used for antibody dilution.
Stop solution: prepared by slowly adding 6 ml of 95%-98% sulfuric acid to 180 ml of water, ready to use when it is cooled down.
Primary antibody: the antibody R66 prepared in the present invention, diluted to a working concentration of 10 μg/ml.
Secondary antibody: Peroxidase-conjugated AffiniPure Goat Anti-Human IgG (H+L) (purchased from Jackson Immuno Research), completely dissolved with 1.5 ml of RNase-free water for use.

To prepare coating antigen solution, RSV-F (Strain A2) and RSV-F (Strain RSS-2) (purchased from Sino Biological Inc.) were diluted with PBS (1×) (pH 7.4) buffer to the final concentration of 2 ng/μl. 100 μl of the coating antigen solution was pipetted into each well of a 96-well plate, coated overnight at 2-8° C., and washed 5 times with PBST, then each well was added with 200 μl of blocking solution for blocking for 2 hours at 37° C., and washed 5 times with PBST for 1 minute each wash after completion of blocking.

The primary antibody was diluted 10 times with an antibody diluent (PBST+1% BSA): i.e., 7 autoclaved 1.5 ml centrifuge tubes were taken, 270 μl of antibody diluent was added to each tube, and 30 μl of primary antibody was taken from the working solution, the resulting mixture was vortexed and mixed, labeled as 1:10 diluent; 30 μl was taken from the 1:10 diluent into the next tube, and 1:10, 1:100, 1:1000, 1:10,000, 1:100,000, 1:1,000,000, 1:10,000,000 diluents were successively obtained in a similar fashion, which were added into the corresponding well with 100 μl per well. Two parallel experiments were performed, and two blank wells were set up to replace the primary antibody with PBST, incubated for 90 minutes at 37° C. and then washed 5 times with PBST.

The secondary antibody was diluted 5,000 times with the antibody diluent (PBST+1% BSA). 100 μl of diluent was added to each well, incubated for 1 hour at 37° C., then washed 5 times with PBST, added with TMB substrate solution with 100 μl/well, incubated for 15 minutes at room temperature. After the completion of the incubation $H_2SO_4$ stop solution was added to terminate the reaction. The absorbance of $OD_{450}$ was read on the microplate reader.

The above ELISA results were analyzed by GraphPad Prism software to obtain the $EC_{50}$ values of the antibody R66 and the Synagis antibody.

The results showed that the binding of the expressed and purified antibody R66 to RSV-F (Strain A2) and RSV-F (Strain RSS-2) is dose-dependent, indicating that the binding of antibody R66 to RSV-F (Strain A2) and RSV-F (Strain RSS-2) is specific.

Figure 2:
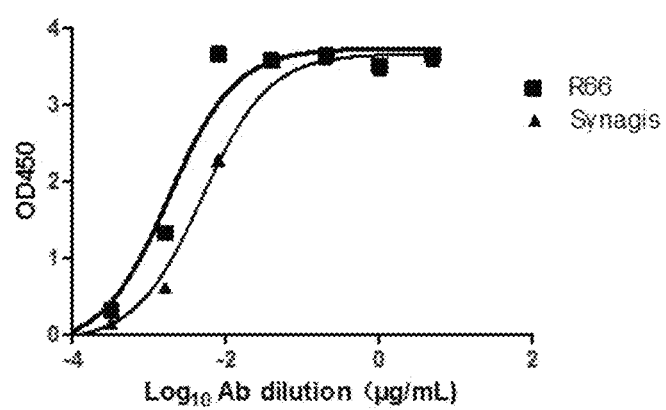
FIG. 2 shows an ELISA test for detecting the binding of monoclonal antibody R66 to RSV-F (Strain A2)
Figure 3:
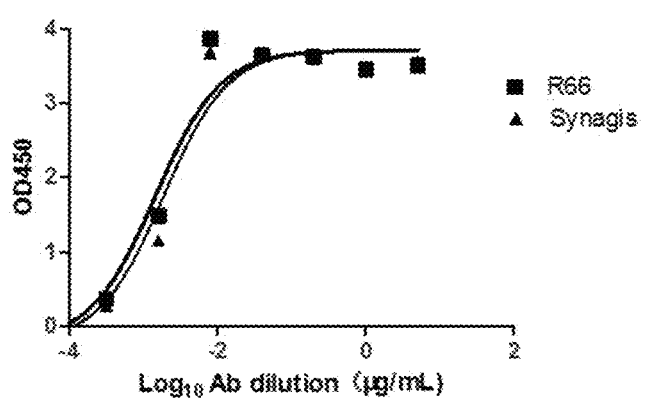
FIG. 3 shows an ELISA test for detecting the binding of monoclonal antibody R66 to RSV-F (Strain RSS-2)

As can be seen from FIG. 2, the $EC_{50}$ value of the R66 antibody to RSV-F (Strain A2) is 1.791 ng/mL, which is lower than that of Synagis (4.881 ng/mL, determined by performing ELISA with Synagis under the same conditions and analyzing with GraphPad Prism software). As can be seen from FIG. 3, the $EC_{50}$ value of the R66 antibody to RSV-F (Strain RSS-2) is 1.463 ng/mL, which is also lower than that of Synagis (1.878 ng/mL, determined by performing ELISA with Synagis under the same conditions and analyzing with GraphPad Prism software). This shows that the antibody R66 of the present invention has higher affinity than Synagis.

Example 4 Determination of CDRs of Monoclonal Antibody R66: Determination of Heavy Chain CDR and Light Chain CDR of the Monoclonal Antibody R66

Figure 4:
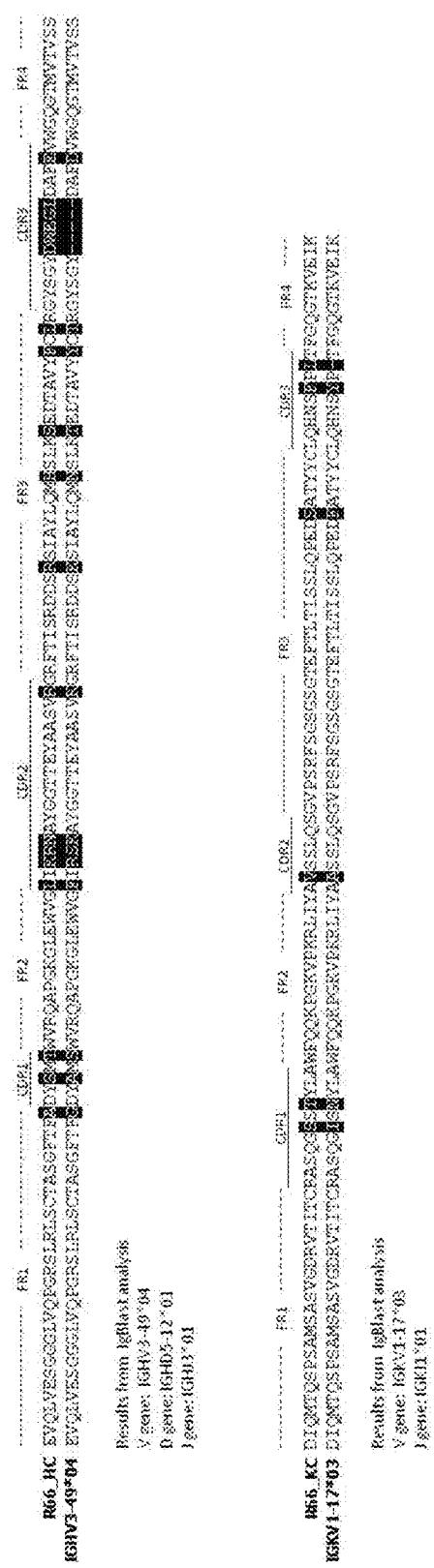
FIG. 4 shows the analysis result of CDR of monoclonal antibody R66, wherein R66_HC is the heavy chain of R66 and R66_KC is the light chain of R66.

The variable region sequence information of the antibody was imported into the IgBLAST program (version 1.6.1) for alignment with library of the human variable region original sequence. The variable region of the antibody was further determined into 3 framework regions (FRs) and 2 complementary determinant regions (CDRs). The antibody sequences were then imported into the IMGT High V-Quest system to identify the CDR3 and FR4 using the same library as before for alignment. All the numberings of the antibody sequences are based on the KABAT system. The analysis and alignment results are shown in FIG. 4.

The results showed that the amino acid sequences of the CDR1, CDR2, and CDR3 of heavy chain of monoclonal antibody are SEQ ID NO: 6, SEQ ID NO: 8, and SEQ ID NO: 10, respectively, and the corresponding nucleotide sequences thereof are SEQ ID NO: 5, SEQ ID NO: 7, and SEQ ID NO: 9, respectively; the amino acid sequences of the CDR1, CDR2, and CDR3 of light chain are SEQ ID NO: 12, SEQ ID NO: 14, and SEQ ID NO: 16, respectively, and the corresponding nucleotide sequences thereof are SEQ ID NO: 11, SEQ ID NO: 13, and SEQ ID NO: 15, respectively.

It should be understood that the above specific embodiments of the present invention are only used to exemplify or explain the principle of the present invention, but not to limit the present invention. Therefore, any modification, equivalent replacement, and improvement made without departing from the spirit and scope of the present invention shall fall within the protection scope of the present invention. Furthermore, the appended claims of the present invention are intended to cover all changes and modifications that fall within the scope and the borderline of the appended claims, or the equivalents of such scopes and boundaries.

The invention claimed is:

1. An anti-RSV antibody or antigen-binding fragment thereof, wherein the antibody comprises: three heavy chain CDRs comprising SEQ ID NO: 6, SEQ ID NO: 8, and SEQ ID NO: 10; and three light chain CDRs comprising SEQ ID NO: 12, SEQ ID NO: 14, and SEQ ID NO: 16.

2. The antibody or antigen-binding fragment thereof of claim 1, wherein the antibody comprises:
a heavy chain variable region having the amino acid sequence as shown in SEQ ID NO: 3 and/or a light chain variable region having the amino acid sequence as shown in SEQ ID NO: 4.

3. The antibody or antigen-binding fragment thereof of claim 1, wherein the antigen-binding fragment is selected from the group consisting of Fab, Fab', F(ab)2, single chain Fv(scFv), Fv, dsFv, diabody, Fd, and Fd' fragments.

4. A single domain antibody, chimeric antibody, antibody fusion protein, antibody/antibody fragment-factor fusion protein or antibody/antibody fragment-chemical conjugate, comprising the single heavy chain, the single light chain or the antigen-binding fragment of the antibody of claim 1.

5. The single domain antibody, chimeric antibody, antibody fusion protein, antibody/antibody fragment-factor fusion protein or antibody/antibody fragment-chemical conjugate of claim 4, wherein the antibody comprises:
three heavy chain CDRs selected from those having the amino acid sequences shown in SEQ ID NO: 6, SEQ ID NO: 8, and SEQ ID NO: 10; and/or
three light chain CDRs selected from those having the amino acid sequences shown in SEQ ID NO: 12, SEQ ID NO: 14, and SEQ ID NO: 16.

6. The single domain antibody, chimeric antibody, antibody fusion protein, antibody/antibody fragment-factor fusion protein or antibody/antibody fragment-chemical conjugate of claim 4, wherein the antibody comprises:
a heavy chain variable region having the amino acid sequence as shown in SEQ ID NO: 3 and/or a light chain variable region having the amino acid sequence as shown in SEQ ID NO: 4.

7. The single domain antibody, chimeric antibody, antibody fusion protein, antibody/antibody fragment-factor fusion protein or antibody/antibody fragment-chemical conjugate of claim 4, wherein the antigen-binding fragment is selected from the group consisting of Fab, Fab', F(ab)$_2$, single chain Fv(scFv), Fv, dsFv, diabody, Fd, and Fd' fragments.

8. A pharmaceutical composition for treating RSV-associated diseases comprising a therapeutically effective amount of the antibody or antigen-binding fragment thereof of claim 1, and one or more pharmaceutically acceptable carriers or excipients.

9. The pharmaceutical composition of claim 8, wherein the antibody comprises:
   three heavy chain CDRs selected from those having the amino acid sequences shown in SEQ ID NO: 6, SEQ ID NO: 8, and SEQ ID NO: 10; and/or
   three light chain CDRs selected from those having the amino acid sequences shown in SEQ ID NO: 12, SEQ ID NO: 14, and SEQ ID NO: 16.

10. The pharmaceutical composition of claim 8, wherein the antibody comprises:
   a heavy chain variable region having the amino acid sequence as shown in SEQ ID NO: 3 and/or a light chain variable region having the amino acid sequence as shown in SEQ ID NO: 4.

11. The pharmaceutical composition of claim 8, wherein the antigen-binding fragment is selected from the group consisting of Fab, Fab', F(ab)$_2$, single chain Fv(scFv), Fv, dsFv, diabody, Fd, and Fd' fragments.

12. The pharmaceutical composition of claim 8, wherein the RSV-associated disease is selected from the group consisting of viral pneumonia, interstitial pneumonia, and bronchiolitis.

\* \* \* \* \*

SEQUENCE LISTING

```
<160> NUMBER OF SEQ ID NOS: 16

<210> SEQ ID NO 1
<211> LENGTH: 378
<212> TYPE: DNA
<213> ORGANISM: Homo sapiens

<400> SEQUENCE: 1
gaggtgcagc tggtggagtc tgggggaggc ttggtacagc cagggcggtc cctgagactc      60
tcctgtacag cttctggatt caccttttgct gattattcta tgacttgggt ccgccaggct     120
ccaggaaagg ggctggagtg ggtaggtctc attaaaagga atgcttatgg tgggaccaca     180
gaatacgccg cgtctgtgag aggcagattc accatctcaa gagatgattc cagaagcatc     240
gcctatctac aaatgcacag cctgaaaagt gaggatacag ccgtctattt ctgtcttcga     300
ggatatagtg gctatgattg ggaaggtctt gatgcttttg aagtctgggg ccaagggaca     360
```
atggtcaccg tctcttca                                                         378

<210> SEQ ID NO 2
<211> LENGTH: 321
<212> TYPE: DNA
<213> ORGANISM: Homo sapiens

<400> SEQUENCE: 2
gacatccaga tgacccagtc tccatctgcc atgtctgcat ctgtaggaga cagggtcacc    60
atcacttgtc gggcgagtca gggcagtagc acttatttag cctggtttca gcagaaacca   120
gggaaagtcc ctaagcgcct gatctatgct gtatccagtt tgcaaagtgg ggtcccatca   180
aggttcagcg gcagtggatc tgggacagaa ttcactctca caatcagcag cctgcagcct   240
gaagattctg caacttatta ctgtctacaa cataatagtt cccgttgac gttcggccaa    300 gggaccaagg tggagatcaa a                                              321

<210> SEQ ID NO 3
<211> LENGTH: 126
<212> TYPE: PRT
<213> ORGANISM: Homo sapiens

<400> SEQUENCE: 3

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Ala Asp Tyr
            20                  25                  30

Ser Met Thr Trp Val Arg Gln Ala Pro Gly Lys Gly Leu Glu Trp Val
        35                  40                  45

Gly Leu Ile Lys Arg Asn Ala Tyr Gly Gly Thr Thr Glu Tyr Ala Ala
    50                  55                  60

Ser Val Arg Gly Arg Phe Thr Ile Ser Arg Asp Asp Ser Arg Ser Ile
65                  70                  75                  80

Ala Tyr Leu Gln Met His Ser Leu Lys Ser Glu Asp Thr Ala Val Tyr
                85                  90                  95

Phe Cys Leu Arg Gly Tyr Ser Gly Tyr Asp Trp Glu Gly Leu Asp Ala
            100                 105                 110

Phe Glu Val Trp Gly Gln Gly Thr Met Val Thr Val Ser Ser
        115                 120                 125

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ala Met Ser Ala Ser Val Gly
1               5                   10                  15

Asp Arg Val Thr Ile Thr Cys Arg Ala Ser Gln Gly Ser Ser Thr Tyr
            20                  25                  30

Leu Ala Trp Phe Gln Gln Lys Pro Gly Lys Val Pro Lys Arg Leu Ile
        35                  40                  45

Tyr Ala Val Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ser Ala Thr Tyr Tyr Cys Leu Gln His Asn Ser Phe Pro Leu
                85                  90                  95

Thr Phe Gly Gln Gly Thr Lys Val Glu Ile Lys
            100                 105

<210> SEQ ID NO 5
<211> LENGTH: 15
<212> TYPE: DNA
<213> ORGANISM: Homo sapiens

<400> SEQUENCE: 5
gattattcta tgact                                                    15

<210> SEQ ID NO 6
<211> LENGTH: 5
<212> TYPE: PRT
<213> ORGANISM: Homo sapiens

<400> SEQUENCE: 6

Asp Tyr Ser Met Thr
1               5

<210> SEQ ID NO 7
<211> LENGTH: 57
<212> TYPE: DNA
<213> ORGANISM: Homo sapiens

<400> SEQUENCE: 7
ctcattaaaa ggaatgctta tggtgggacc acagaatacg ccgcgtctgt gagaggc      57

<210> SEQ ID NO 8
<211> LENGTH: 19
<212> TYPE: PRT
<213> ORGANISM: Homo sapiens

<400> SEQUENCE: 8

Leu Ile Lys Arg Asn Ala Tyr Gly Gly Thr Thr Glu Tyr Ala Ala Ser
1               5                   10                  15

Val Arg Gly

<210> SEQ ID NO 9
<211> LENGTH: 45
<212> TYPE: DNA
<213> ORGANISM: Homo sapiens

<400> SEQUENCE: 9
ggatatagtg gctatgattg ggaaggtctt gatgcttttg aagtc                   45

<210> SEQ ID NO 10
<211> LENGTH: 15
<212> TYPE: PRT
<213> ORGANISM: Homo sapiens

<400> SEQUENCE: 10

Gly Tyr Ser Gly Tyr Asp Trp Glu Gly Leu Asp Ala Phe Glu Val
1               5                   10                  15

<210> SEQ ID NO 11
<211> LENGTH: 33
<212> TYPE: DNA
<213> ORGANISM: Homo sapiens

<400> SEQUENCE: 11
cgggcgagtc agggcagtag cacttattta gcc                                33

```
<210> SEQ ID NO 12
<211> LENGTH: 11
<212> TYPE: PRT
<213> ORGANISM: Homo sapiens

<400> SEQUENCE: 12

Arg Ala Ser Gln Gly Ser Ser Thr Tyr Leu Ala
1               5                   10

<210> SEQ ID NO 13
<211> LENGTH: 21
<212> TYPE: DNA
<213> ORGANISM: Homo sapiens

<400> SEQUENCE: 13
gctgtatcca gtttgcaaag t                                         21

<210> SEQ ID NO 14
<211> LENGTH: 7
<212> TYPE: PRT
<213> ORGANISM: Homo sapiens

<400> SEQUENCE: 14

Ala Val Ser Ser Leu Gln Ser
1               5

<210> SEQ ID NO 15
<211> LENGTH: 27
<212> TYPE: DNA
<213> ORGANISM: Homo sapiens

<400> SEQUENCE: 15
ctacaacata atagtttccc gttgacg                                   27

<210> SEQ ID NO 16
<211> LENGTH: 9
<212> TYPE: PRT
<213> ORGANISM: Homo sapiens

<400> SEQUENCE: 16

Leu Gln His Asn Ser Phe Pro Leu Thr
1               5
```